United States Patent
Hohner et al.

(10) Patent No.: US 6,550,312 B1
(45) Date of Patent: Apr. 22, 2003

(54) METHOD FOR DETERMINING THE AIR/FUEL RATIO IN AN INTERNAL COMBUSTION ENGINE COMBUSTION CHAMBER

(75) Inventors: Peter Hohner, Leinfelden-Echterdingen (DE); Jürgen Schenk, Albershausen (DE); Hartung Wilstermann, Bammental (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/522,971

(22) Filed: Mar. 10, 2000

(30) Foreign Application Priority Data

Mar. 12, 1999 (DE) .......................................... 199 11 019

(51) Int. Cl.$^7$ ............................................. G01M 15/00
(52) U.S. Cl. ..................................... 73/35.08; 73/117.3
(58) Field of Search .............................. 73/35.08, 35.01, 73/35.03, 35.06, 35.07, 116, 117.2, 117.3

(56) References Cited

U.S. PATENT DOCUMENTS

| | | | |
|---|---|---|---|
| 5,687,082 A | * | 11/1997 | Rizzoni ..................... 73/117.3 |
| 5,954,024 A | * | 9/1999 | Duhr et al. |
| 6,006,157 A | * | 12/1999 | Dai et al. |
| 6,029,627 A | * | 2/2000 | VanDyne ..................... 73/116 |
| 6,089,077 A | * | 7/2000 | Daniels ..................... 73/35.08 |
| 6,092,015 A | * | 7/2000 | Takahashi et al. ......... 73/35.08 |
| 6,104,195 A | * | 8/2000 | Yoshinaga et al. ......... 73/35.08 |

FOREIGN PATENT DOCUMENTS

| | | |
|---|---|---|
| DE | 2449836 C | 10/1974 |
| DE | 2554988 | 12/1975 |
| DE | 2932193 | 8/1979 |
| DE | 2935725 | 9/1979 |
| DE | 2939690 A1 | 9/1979 |
| DE | 3445539 C2 | 12/1984 |
| DE | 4239803 C2 | 11/1992 |
| DE | 19614388 C1 | 4/1996 |
| DE | 19735454 A1 | 8/1997 |

* cited by examiner

*Primary Examiner*—Eric S. McCall
(74) *Attorney, Agent, or Firm*—Crowell & Moring LLP

(57) ABSTRACT

A method for determining the air/fuel ratio in an internal combustion engine combustion chamber having at least two ignition plugs spaced apart from one another. Ion-current measurement is carried out during successive operating cycles, wherein a first ignition plug is operated as an ion-current sensor and does not release ignition energy. The time of arrival at the first ignition plug of a flame front formed at the ignition point of a second ignition plug, is detected. The detected time of arrival of the flame front, the ignition point and the ignition-plug spacing are used to determine the speed of the flame and, from this, the air/fuel ratio is determined as a function of the speed and/or load of the internal combustion engine.

8 Claims, 2 Drawing Sheets

METHOD FOR DETERMINING THE AIR/FUEL RATIO IN AN INTERNAL COMBUSTION ENGINE COMBUSTION CHAMBER

CROSS REFERENCE TO RELATED APPLICATIONS

Priority is claimed under 35 U.S.C. §119 with respect to German Patent Application No. 199 11 019.0-52 filed on Mar. 12, 1999.

BACKGROUND OF THE INVENTION

The invention relates to a method for determining the air/fuel ratio in an internal combustion engine combustion chamber having at least two ignition plugs spaced apart from one another, as used, for example, for motor vehicles.

German preliminary published application DE 25 54 988 A1 has disclosed the arrangement of an ion-current sensor in the exhaust system downstream of the exhaust valves of a combustion chamber of an internal combustion engine. With the aid of the ion-current sensor positioned in this way, measurement of the ion current of the combustion products is performed and a controlled variable is generated for a mixture-forming device and an ignition device. Mixture formation and ignition setting are then controlled as a function of the operating state of the internal combustion engine.

German Patent DE 42 39 803 C2 has disclosed an ionization-current detector for an internal combustion engine in which an ignition plug in a combustion chamber of the internal combustion engine is used both to initiate combustion and to detect complete combustion of the combustion-chamber charge and thus to detect misfires.

German Patent DE 196 14 388 C1 has disclosed a method for determining the quality of an air/fuel mixture in a combustion chamber of an internal combustion engine. Here a test pulse is applied to an ignition plug, which is initially used to generate a customary ignition pulse, after the ignition of the air/fuel mixture. The test pulse comprises a voltage pulse which remains constant for a prolonged period during the combustion phase to be investigated and is applied to the ignition plug via a measuring resistor. At the measuring resistor it is possible to measure avoltage drop which changes with the ion current at the ignition plug and the integral of which is used as a measure of the composition of the mixture in the combustion chamber.

German preliminary published application DE 29 39 690 A1 has disclosed a method for controlling the ignition point for an internal combustion engine. In this method, an ion-current sensor is arranged at a distance from an ignition point in a combustion chamber of the internal combustion engine. The ion-current sensor is used to monitor the ignition of the combustion-chamber charge, the end of an initial ignition phase of the combustion-chamber charge being kept in a particular relationship with top dead centre. To carry out the method, one or two ion-current sensors are arranged around the ignition electrodes of the ignition plug, the ion-current sensors being combined with the ignition plug.

German Patent DE 34 45 539 C2 has disclosed an ionization sensor for controlling the combustion process in a combustion chamber of an internal combustion engine. The ionization sensor is arranged in the combustion chamber at a distance from the location of ignition, allowing it to detect the arrival of a flame front, and the quality of the combustion process which takes place is determined from the time which elapses between ignition of the air/fuel mixture in the combustion chamber and the arrival of the flame front at the sensor.

German preliminary published application DE 29 35 725 A1 has disclosed an apparatus for adjusting the ignition point of an internal combustion engine with applied ignition. It comprises a first ionization sensor at a relatively large distance from an ignition plug and optionally a second ionization sensor close to the ignition plug. In particular, the second ionization sensor is used to detect the beginning of combustion and the first ionization sensor is used to detect the end of combustion. The ignition point of the internal combustion engine is adjusted as a function of the signals detected.

German preliminary published application DE 29 32 193 A1 has disclosed an apparatus for detecting knock phenomena in a combustion chamber of an internal combustion engine with feedback-controlled ignition. It comprises two ionization sensors, which are arranged in the combustion chamber as far as possible away from an ignition plug for igniting the air/fuel mixture, in a region in which knock phenomena are possible. The two ionization sensors are arranged in the direction of progress of the flame front in the combustion chamber relative to one another and are used to determine the speed of the flame, from which, in turn, conclusions can be drawn about knock phenomena.

It is the object of the invention to determine the air/fuel ratio in a combustion chamber of an internal combustion engine in as simple a manner as possible and as reliably as possible with a method of the type stated at the outset.

SUMMARY OF THE INVENTION

According to the invention, this object is achieved by a method in which a measurement of the speed of the flame in the air/fuel mixture in the combustion chamber is performed between two ignition plugs arranged in a common combustion chamber of the internal combustion engine. A first ignition plug, which is operated as an ion-current sensor, is used to ascertain the time of arrival of the flame front at this ignition plug, while a second ignition plug is used to release ignition energy and to ascertain the ignition point. The air/fuel ratio is determined from the speed of the flame, taking into account the operating point of the internal combustion engine. The ignition plugs are preferably used alternately to release ignition energy and as ion-current sensors. The method proposed can be used to determine the air/fuel ratio individually in each combustion chamber of the internal combustion engine, allowing fuel metering to be performed individually for each combustion chamber and an oxygen sensor in the exhaust duct to be dispensed with.

As a refinement of the invention, in an operating cycle with ion-current measurement, the ignition point of the second ignition plug is advanced in comparison with operating cycles with release of ignition energy and at both ignition plugs and hence without ion-current measurement. Here, release of ignition energy at both ignition plugs is provided, in particular, in full-load operation of the internal combustion engine, and release of ignition energy at just one ignition plug is preferably provided in part-load operation. Advancing the ignition point takes account of the possibility that combustion in the combustion chamber may take place more slowly initially, and displacement of the main focus of combustion towards the rear is avoided.

As a further refinement of the invention, ion-current measurement is performed in each operating cycle in the part-load range of the internal combustion engine, the ignition plugs being operated alternately as ion-current sensors. According to this, each ignition plug functions as an ion-current sensor and does not release ignition energy in one operating cycle and, in the following operating cycle, it functions as an ignition plug which releases ignition energy. This prevents the formation of deposits such as those which can form on an electrode which is used exclusively as an ion-current sensor. It is also possible to make the stressing of the combustion-chamber walls more uniform.

As a further refinement of the invention, ion-current measurement is formed in only some of the operating cycles in the part-load range of the internal combustion engine. Here, the same ignition plug can be operated as an ion-current sensor every time, making evaluation simpler.

BRIEF DESCRIPTION OF THE DRAWINGS

Advantageous embodiments of the invention are illustrated in the drawings and are described below. In this connection.

DETAILED DESCRIPTION OF THE PREFERRED EMBODIMENT

The method illustrated is suitable for an internal combustion engine—of, for example, a motor vehicle—which has at least one combustion chamber with two ignition plugs which are arranged spaced apart from one another and of which at least one can be activated to release ignition energy and at least one can be operated as an ion-current sensor.

In full-load operation of the internal combustion engine, both ignition plugs can be activated to release ignition energy while, in each operating cycle of the internal combustion engine in a part-load mode, one ignition plug can be used to release ignition energy and one can be used as an ion-current sensor which does not release ignition energy.

The internal combustion engine is assigned an engine control unit in which information signals can be called up on the load and speed of the internal combustion engine. The engine control unit determines the ignition point of each combustion chamber of the internal combustion engine and controls the ignition plugs in a corresponding manner. The engine control unit furthermore determines the quantity of fuel to be injected into each individual combustion chamber and the air mass to be introduced, thereby by making it possible to define the air/fuel ratio in the respective combustion chamber.

The internal combustion engine is furthermore assigned a catalytic converter, in particular a three-way catalytic converter, making it expedient to operate the internal combustion engine at a particular, controllable air/fuel ratio, e.g. a stoichiometric air/fuel ratio of $\lambda=1$. For other reasons too, e.g. for reasons of internal pollutant reduction or targeted quality control of the internal combustion engine, as accurate determination of the air/fuel ratio in the combustion chambers of the internal combustion engine as possible may be desirable.

The air/fuel ratio $\lambda$ is determined with the aid of the method according to the invention as follows. During an operating cycle of the internal combustion engine, a first ignition plug operated as an ion-current sensor performs an ion-current measurement by means of which the arrival of the flame front of the combustion process taking place during the operating cycle concerned at this first ignition plug is detected. This first ignition plug is arranged at a defined distance from a second ignition plug, which releases the ignition energy to initialize the combustion process concerned. The second ignition plug can thus be used to obtain a signal which describes the ignition point of the combustion process taking place in the combustion chamber, making it possible to determine the speed of the flame from the difference between the time of arrival of the flame front at the first ignition plug and the ignition point, taking into account the ignition plug spacing. As an option, ion-current measurement can also be performed at the second ignition plug, which releases ignition energy.

Figure 1:
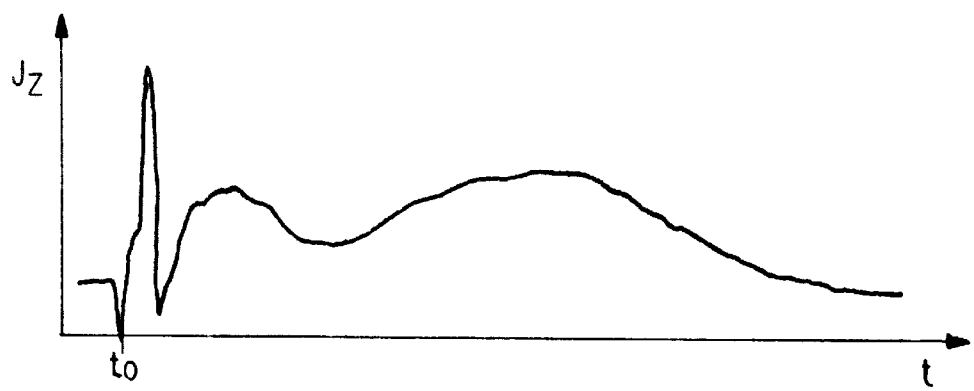
FIG. 1 shows, in an ion current/time diagram, an ion-current signal at an ignition plug releasing ignition energy in a combustion chamber of an internal combustion engine.
Figure 2:
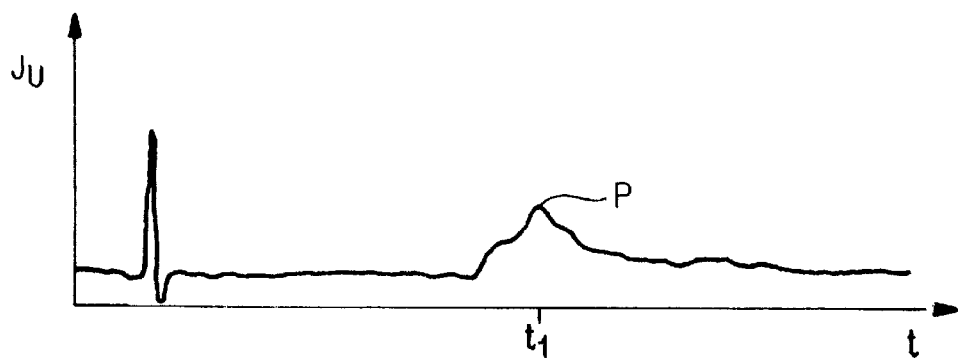
FIG. 2 shows, in an ion-flow/time diagram, an ion-current signal at an ignition plug which is not releasing ignition energy, this ignition plug being spaced apart from the ignition plug which is releasing ignition energy.

Schematic diagrams in FIGS. 1 and 2 illustrate typical ion-current signals $I_z$ and $I_u$ for the two ignition plugs, FIG. 1 illustrating the ion-current signal $I_z$ for the second ignition plug, which releases ignition energy, and FIG. 2 illustrating the ion-current-signal $I_u$ for the first ignition plug, each signal being plotted against the duration t of the combustion process in the combustion chamber. At time $t_0$, the second ignition plug releases the ignition energy for the combustion process in the form of an ignition spark, whereupon a sharp increase in the ion-current signal $I_z$ at the second ignition plug can be recorded, this sharp increase being characteristic of the initialization of the combustion process. There then forms in the combustion chamber a flame front with turbulent flow, which propagates through the combustion chamber. Here, the speed of the flame changes very rapidly in the initial phase of combustion and combustion makes a transition from laminar to turbulent flow. This transition takes place relatively rapidly and is negligible at some distance from the second ignition plug. The first ignition plug, that acting as an ion-current sensor, which is operated without releasing ignition energy, accordingly detects the arrival of the turbulent flame front as a peak value P in its ion-current signal $I_u$ at time $t_1$. The time difference $t_1-t_0$ between the ignition point $t_0$ and the detected time of arrival $t_1$ of the flame front at the first ignition plug represents the time required by the flame front to cross the gap between the two ignition plugs, and it is thus possible to determine the speed of the flame from this.

Figure 3:
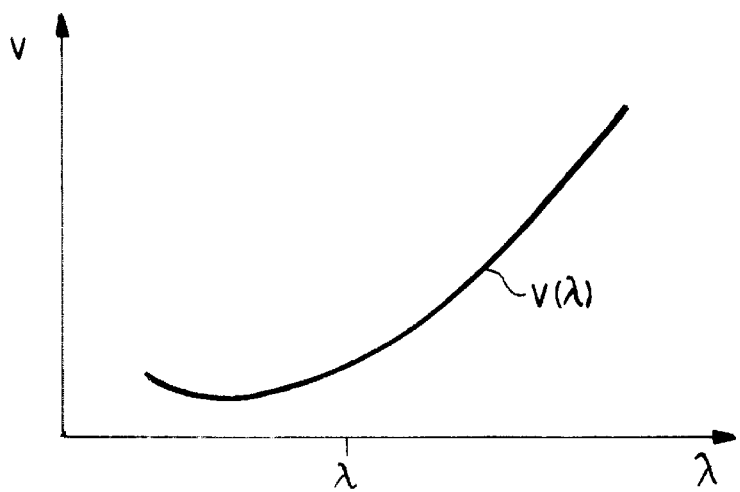
FIG. 3 shows in a function diagram, the dependence of the flame speed on the air/fuel ratio in the combustion chamber of the internal combustion engine.
Figure 4:
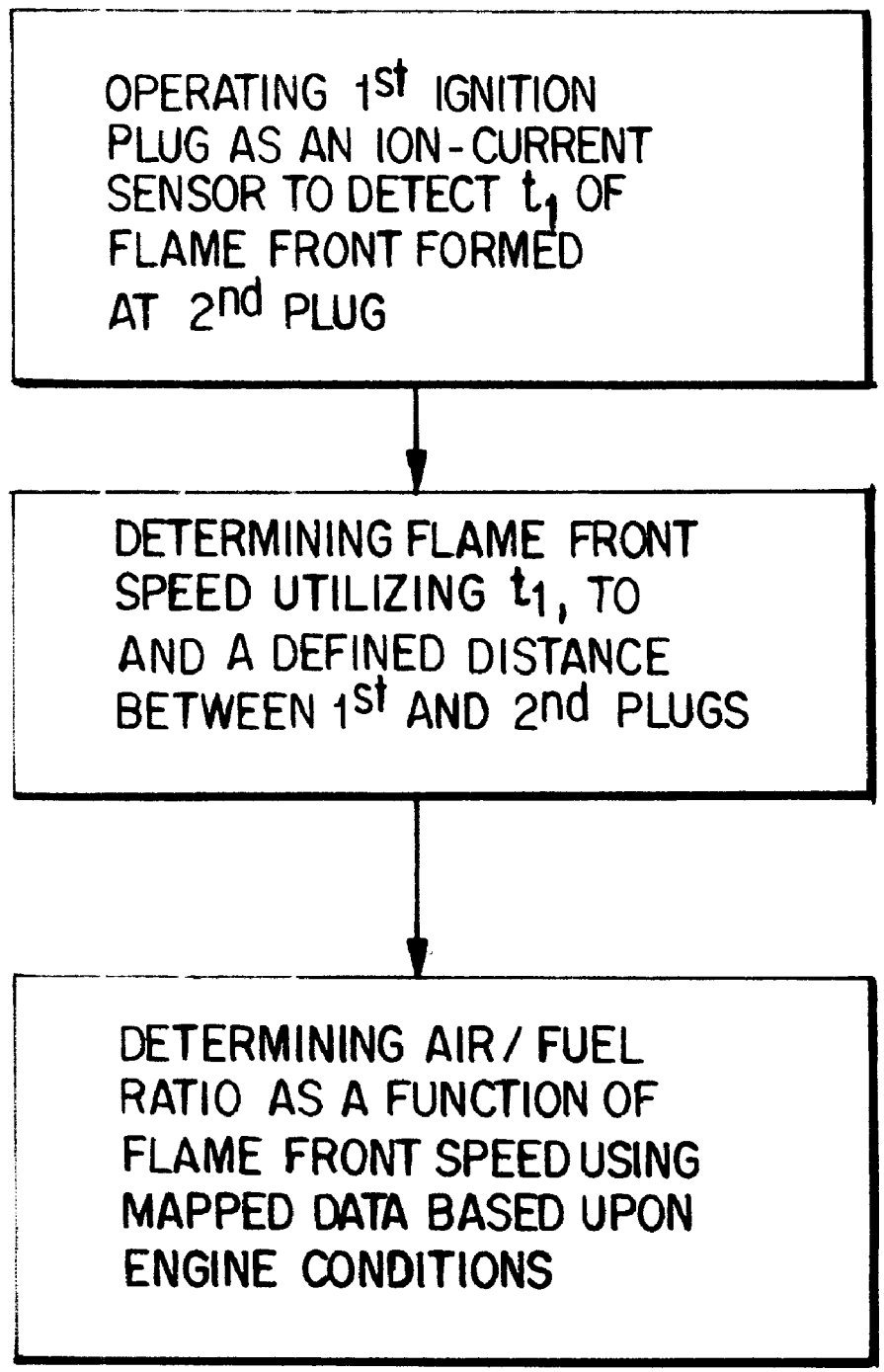
FIG. 4 is a flow diagram showing the steps of the method of the present invention.

FIG. 3 shows the relationship $v(\lambda)$ between the speed of the flame v and the air/fuel ratio $\lambda$ of the combustion-chamber charge for a particular operating point around the stoichiometric value of $\lambda_1=1$. Different but similar relationships between the turbulent speed of the flame v and the air/fuel ratio $\lambda$ are obtained for different operating points of the internal combustion engine, making it possible to produce a characteristic map-dependent, in particular, on the engine speed and load or mean pressure in the combustion chamber—for the relationship between the turbulent speed of the flame v and the air/fuel ratio $\lambda$, from which map the associated air/fuel ratio can in each case be taken once the speed of the flame has been determined.

In normal part-load operation of the internal combustion engine, the first ignition plug is operated as an ion-current sensor at regular intervals, e.g. every tenth operating cycle, and, in this cycle ignition at this ignition plug is suspended.

As an alternative, one ignition plug can be operated as an ion-current sensor in every operating cycle, this preferably taking place alternately at both ignition plugs. Compared with operation of the internal combustion engine involving initiation of the combustion process by both ignition plugs, the ignition point in an operating cycle in which ion-current measurement is carried out while suspending the release of ignition energy by one ignition plug is advanced, thus avoiding displacement of the main focus of combustion and hence a reduction in power or increase in fuel consumption.

In full-load operation of the internal combustion engine, suspension of the release of ignition energy by the first ignition plug when the latter is operated as an ion-current sensor is only performed when and to the extent that it is still possible to achieve the desired power of the internal combustion engine.

In a modified illustrative embodiment, ion-current measurement is carried out in only some of the operating cycles of the internal combustion engine during part-load operation too and the same ignition plug is preferably used as the ion-current sensor. This results in a particularly simple design of the measuring arrangement, the intermittent operation of the first ignition plug preventing permanent soiling of the latter.

By means of the method according to the invention, it is possible to determine and control the air/fuel ratio for each individual combustion chamber of the internal combustion engine, this process being particularly accurate because it can be carried out individually for each operating cycle. There is no need for an oxygen sensor in the exhaust duct, this sensor having only limited functionality and possibly requiring heating, particularly in a cold-start phase of the internal combustion engine. The method proposed allows reliable determination of the air/fuel ratio in a combustion chamber from the first operating cycle onwards, without preheating. The method is suitable not only for internal combustion engines with applied ignition, in which the ignition energy is supplied by ignition sparks, but also for those with self-ignition, in which the ignition-energy-supplying ignition plug in the sense of the present invention is formed by a glow plug.

What is claimed is:

1. A method for determining air/fuel ratio in an internal combustion engine combustion chamber having at least two ignition plugs spaced apart from one another by a defined distance, at least one said ignition plug being operable as an ion-current sensor, said method comprising:

(a) in successive operating cycles of said engine, operating a first ignition plug as an ion-current sensor to detect a time of arrival ($t_1$) at said first ignition plug of a flame front formed at an ignition time ($t_0$) at said second ignition plug spaced by said defined distance from said first ignition plug;

(b) determining the flame front speed as a function of the detected time of arrival ($t_1$), the ignition time ($t_0$), and said defined distance, and (c) determining said air/fuel ratio as a function of said flame front speed and dependent on a determined engine speed and/or engine load using a predetermined map showing air/fuel ratio as a function of flame front speed for different values of engine speed and/or engine load.

2. The method of claim 1, wherein only engine speed is used in step (c).

3. The method of claim 1, wherein only engine load is used in step (c).

4. The method of claim 1, wherein combustion chamber pressure indicative of engine load is used in step (c).

5. The method of claim 1, wherein in each operating cycle of said engine wherein ion-current is measured, the ignition time ($t_0$) of said second ignition plug is advanced in comparison to operating cycles of said engine wherein energy is released at both ignition plugs.

6. The method of claim 1 wherein, when said engine is operating at less than a full load level, one of said ignition plugs is operated as an ion-current sensor in every operating cycle of said engine.

7. The method of claim 6 where said ignition plugs alternate between acting as an ion-current sensor and releasing ignition energy.

8. The method of claim 1 wherein when said engine is operating at less than full load level, an ion-current measurement is performed in less than all of said operating cycles of said engine.

* * * * *